US009474501B2

(12) United States Patent
Perkins et al.

(10) Patent No.: US 9,474,501 B2
(45) Date of Patent: Oct. 25, 2016

(54) HYBRID METHOD BASED ON SIMULATION AND EXPERIMENTAL DATA TO NORMALIZE PET DATA

(71) Applicant: KONINKLIJKE PHILIPS N.V., Eindhoven (NL)

(72) Inventors: Amy Perkins, Philadelphia, PA (US); Manoj Narayanan, Mentor, OH (US); Andreia Maria Araujo Trindade Rodrigues, Veldhoven (NL); Pedro Jorge Da Silva Rodrigues, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/911,472

(22) PCT Filed: Aug. 7, 2014

(86) PCT No.: PCT/IB2014/063763
§ 371 (c)(1),
(2) Date: Feb. 11, 2016

(87) PCT Pub. No.: WO2015/022606
PCT Pub. Date: Feb. 19, 2015

(65) Prior Publication Data
US 2016/0192896 A1    Jul. 7, 2016

Related U.S. Application Data

(60) Provisional application No. 61/866,144, filed on Aug. 15, 2013.

(51) Int. Cl.
*A61B 6/03*  (2006.01)
*A61B 6/02*  (2006.01)
(Continued)

(52) U.S. Cl.
CPC ............... *A61B 6/583* (2013.01); *A61B 6/037* (2013.01); *G01T 1/2985* (2013.01)

(58) Field of Classification Search
CPC ............................... A61B 6/037; A61B 6/583
See application file for complete search history.

(56) References Cited

U.S. PATENT DOCUMENTS 7,449,681 B1    11/2008 Rappoport et al.
2005/0242288 A1    11/2005 Wollenweber et al.
(Continued)

FOREIGN PATENT DOCUMENTS

WO    2006/049523    5/2006

OTHER PUBLICATIONS

Wang, et al., "A New Component Approach Efficiency Normalization for 3D PET", 2005 IEEE Nuclear Science Symposium Conference Record, M11-303, 2005.
(Continued)

*Primary Examiner* — Mark R Gaworecki (57) ABSTRACT

A medical system (28) for normalization correction of an imaging system (10) includes a detector geometry correction unit (44), a crystal efficiency unit (46), and a normalization unit (54). The detector geometry correction unit (44) mathematically calculates a detector geometry correction component for a type of scanner (12) of interest. The crystal efficiency unit (46) configured to empirically determine a crystal efficiency component for at least one individual scanner (12). The normalization unit (54) generates a normalization data set (56) which corresponds to a normalization correction factor of the at least one individual scanner (12) in accordance with the detector geometry correction component and the crystal efficiency component.

17 Claims, 5 Drawing Sheets

(51) Int. Cl.
*A61B 6/00* (2006.01)
*G01T 1/29* (2006.01)

(56) References Cited

U.S. PATENT DOCUMENTS

2007/0176087 A1 8/2007 Wang
2009/0314933 A1 12/2009 Breuer et al.
2011/0135179 A1 6/2011 Ross et al.
2012/0076371 A1 3/2012 Caruba et al.

OTHER PUBLICATIONS

Pepin, et al., "Normalization of Monte Carlo PET data using GATE", Nuclear Science Symposium and Medical Imaging conference (NSS.MIC), 2011 IEEE, Oct. 23, 2011.

HYBRID METHOD BASED ON SIMULATION AND EXPERIMENTAL DATA TO NORMALIZE PET DATA

CROSS REFERENCE TO RELATED APPLICATIONS

This application is the U.S. National Phase application under 35 U.S.C. §371 of International Application No. PCT/IB2014/063763, filed Aug 7, 2014, published as WO 2015/022606 on Feb 19, 2015, which claims the benefit of U.S. Provisional Patent Application Number 61/866,144 filed Aug 15, 2013. These applications are hereby incorporated by reference herein.

The following relates generally to medical imaging. It finds particular application in conjunction with calibrating positron emission tomography (PET) scanning, and will be described with particular reference thereto. However, it will be understood that it also finds application in other usage scenarios and is not necessarily limited to the aforementioned application.

In PET imaging, a subject is injected with a radiopharmaceutical which targets particular tissues typically through absorption based on a metabolic activity. As the radiopharmaceutical decays, positrons are emitted which annihilate in contact with an electron to form a pair of photons emitted 180° opposite along a line of response (LOR). PET scanners require normalization to correct for differences in detector sensitivity for different lines of response due to scanner geometry and differences in crystal efficiencies. Inaccuracies in normalization can result in artifacts, poor uniformity and an increase in noise of images produced by the scanner. Normalization correction is typically calculated for each individual scanner and is performed with a phantom, or multiple phantoms, measured on each PET scanner. For example, one normalization correction method utilizes a uniform cylinder and a planar source phantom, both of which are filled with a radioisotope commonly used in PET tracers, e.g., F18, Ge68, and the like. This method takes relatively long acquisition time, e.g., 2-4 hours, with a uniform cylinder, followed by, e.g., 4-6 hours, for a planar source phantom. From these different acquisitions, detector geometry and crystal efficiency components of normalization are calculated.

Component efficiency normalization is generally preferred as accommodating statistical noise and phantom geometry issues. Component efficiency normalization is categorized by the decomposition of detector normalization into discrete factors (or components), with each factor being calibrated individually. For example, component efficiency normalization can be modeled by two categories of factors: detector geometry factors and crystal efficiency factors. Detector geometry factors include circular detector geometry and solid angle, gamma ray incident angle, dead-time, and crystal depth of interaction. Crystal efficiency normalization is necessitated by the non-uniform response of detector crystals and their related light sensitive elements.

The normalization correction for a scanner may be sensitive to small errors in phantom position, which may introduce errors into the corrections. The acquisition time, as noted above, is relatively long for these multiple scans, not only for the scanning itself, but also in setting up the phantoms to achieve very accurate positioning. In some instances, the normalization correction found may be inconsistent causing the phantom to be repositioned and the calibration to be repeated, substantially increasing the time spent determining suitable normalization for a particular scanner. That is, for scanners in a clinical setting with heavy workloads, the down time for regenerating the normalization correction can be burdensome.

Certification of scanners is critical to many sites with PET scanning operations, and this certification process involves full calibration of the scanner, including normalization. Normalization corrections are important in quantitative accuracy. The certification process may lead to recalibrations of scanners when such scanners do not meet predetermined acceptance criteria. A support service may be contacted to facilitate the repair or recalibration and normalization of the scanner to address these issues. Generally, the main issue for which the support service may be called relates to detector geometry.

The following discloses a new and improved method of PET normalization correction which addresses the above referenced issues, and others.

In accordance with one aspect, a medical system for normalization correction of an imaging system that includes a detector geometry correction unit which mathematically calculates a detector geometry correction component for a type of scanner of interest. The medical system also includes a crystal efficiency unit configured to empirically determine a crystal efficiency component for at least one individual scanner. Additionally, the medical system includes a normalization unit which generates a normalization data set corresponding to a normalization correction factor of the at least one individual scanner in accordance with the detector geometry correction component and the crystal efficiency component.

In accordance with another aspect, a method for normalization correction of an imaging system includes generating a detector geometry correction component for a type of scanner of interest. The method further includes empirically determining a crystal efficiency component for at least one individual scanner of the scanner type of interest. In addition, the method includes outputting at least one normalization correction factor for the at least one individual scanner in accordance with the detector geometry correction component and the crystal efficiency component.

In accordance with another aspect, a system includes a first model which is mathematically calculated based on geometric characteristics of a type of scanner of interest, and a second model which is mathematically calculated based on geometry of a calibration phantom. The system further includes a processor configured to generate normalization correction factors for an individual scanner based on crystal efficiency data collected by the individual scanner from a phantom and the first and second models.

One advantage is a reduction in time spent calibrating imaging systems.

Another advantage resides in the precise phantom positioning available via simulation.

Another advantage resides in the generation of a mathematical model of scanner geometry that can be reused during maintenance and setup of the scanner.

Another advantage includes the application of determined normalization correction across all same scanner geometries, i.e., across same models of detector geometries.

In accordance with such application, another advantage is a reduction in certification and calibration times for subsequent scanners utilizing the same geometries.

Another advantage resides in improvement in the quantitative accuracy of the scanner resulting from normalization corrections.

Another advantage resides in the reduction of the number of scans needed to acquire normalization correction factors.

Another advantage includes the improvement in accuracy of PET images.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
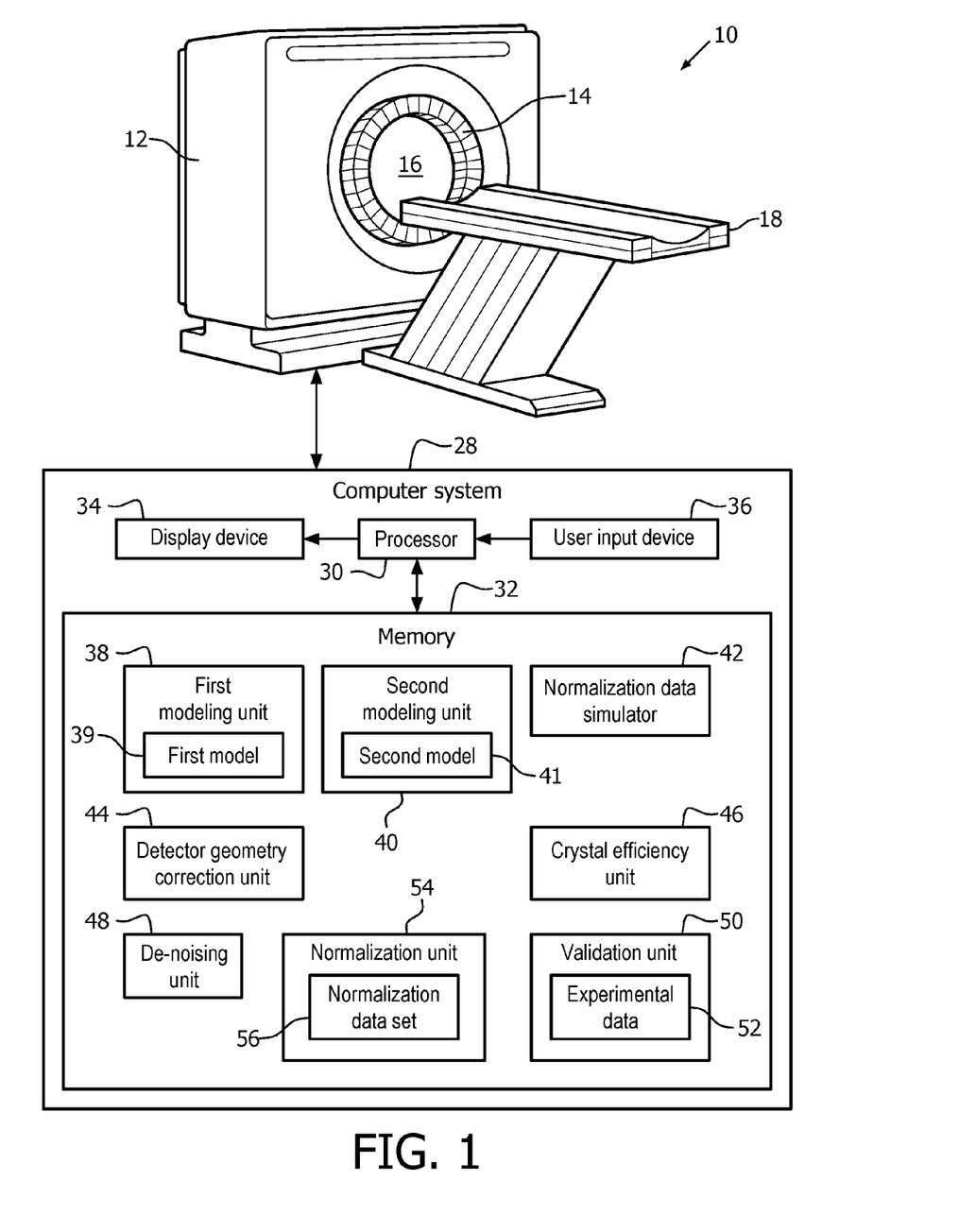
FIG. 1 schematically illustrates an embodiment of a PET scanner in which normalization correction is used.

With reference to FIG. 1, a PET imaging system 10 includes a scanner 12 to generate raw PET data. The scanner 12 includes detectors 14, such as solid state detectors, arranged around a bore of the scanner 12. The bore defines an examination region 16 for receiving a region of interest (ROI), such as a brain, of a subject to image. The detectors 14 are typically arranged in a stationery ring. However, rotatable heads in a partial ring or planar configuration are also contemplated. The scanner 12 can be mounted on tracks to facilitate patient access. The tracks extend in parallel to a longitudinal axis of a subject support 18 carrying a subject to image. A motor and drive or the like provides longitudinal movement and vertical adjustment of the subject support 18 in the examination region 16.

Figure 2:
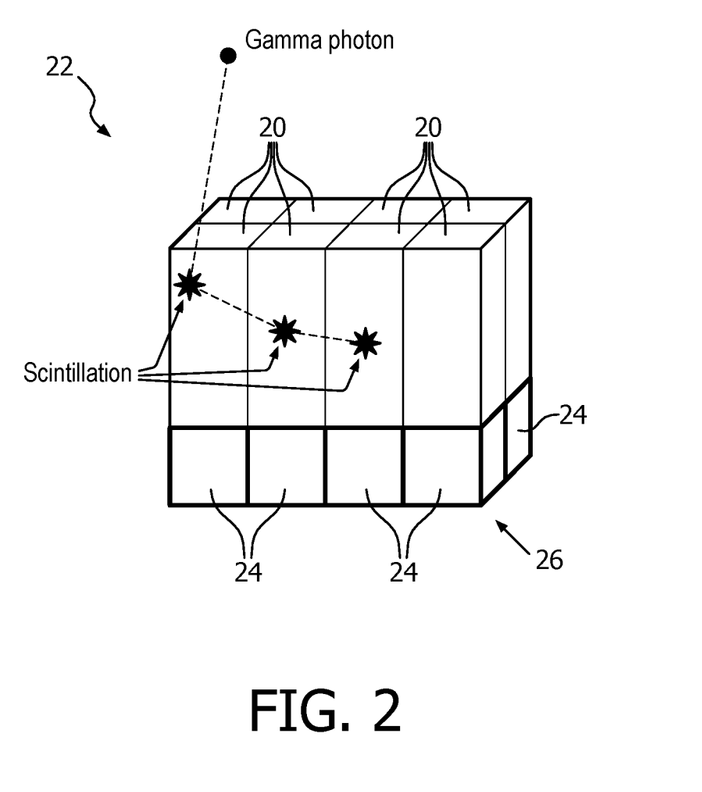
FIG. 2 illustrates detector elements and scintillation crystals of PET detectors.

The detectors 14 detect gamma photons from the examination region 16. With reference to FIG. 2, each of the detectors 14 typically include one or more scintillator crystals 20 arranged in a grid 22 and one or more light sensitive elements 24, e.g., avalanche photodiodes (APD), silicon photomultipliers (SiPMs), photomultiplier tubes, etc. There is typically a one-to-one correspondence between the scintillator crystals 20 and the light sensitive elements 24 (as illustrated), but there can be a one-to-many correspondence therebetween or a many-to-one correspondence therebetween. FIG. 2 shows a typical indirect radiation measurement scheme, but direct radiation detection schemes such as the ones using a direct conversion material like cadmium zinc telluride (CZT) and others can be grouped as well in a structure similar to 14. A plurality of detectors 14 may be manufactured together as a tile. A plurality of tiles can be mounted together to form a module. The module can be mounted to stationary rings around the examination region. To facilitate manufacturing and assembly, the tiles and modules can be fabricated on flat support/cooking panels.

With the usual indirect radiation detection schemes, the scintillator crystals 20 receive gamma photons from the examination region 16. As the gamma photons deposit energy in the scintillator crystals 20, the scintillator crystals 20 scintillate and emit light towards the light sensitive elements 24. The amount of light created by a scintillation event is directly correlated to the amount of energy deposited. The light sensitive elements 24 detect the light emitted by the scintillation crystals 20. Examples of scintillator crystals 20 include sodium iodide doped with thallium (NaI(Tl)), bismuth germanium oxide (BGO), cerium-doped lutetium yttrium orthosilicate (LYSO) and cerium doped lutetium oxyorthosilicate (LSO). Examples of light sensitive elements 24 include photomultiplier tubes (PMTs), photodiodes, avalanche photodiodes (APDs), and solid state photomultipliers (SiPMs).

Figure 5:
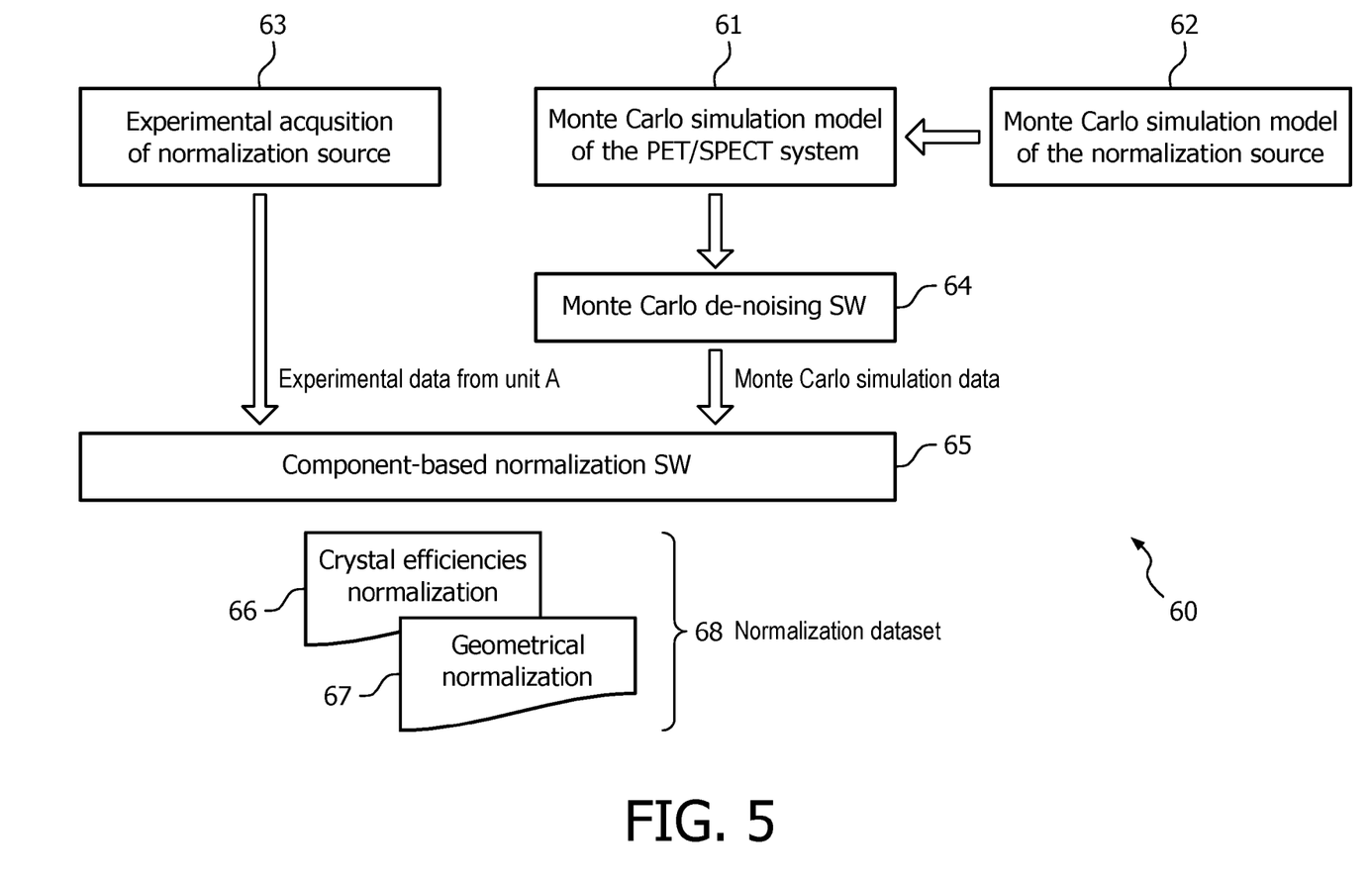
FIG. 5 is a functional block diagram illustrating one embodiment for normalization correction of a scanner in accordance with the systems and methods set forth herein FIG. 6 flowcharts one embodiment of the method for determining normalization correction of an imaging system.

Referring back to FIG. 1 and with reference further to FIG. 5, the system 10 includes a computer system 28 that includes at least a processor 30 in communication with a memory 32. The memory 32 includes processed data, such as experimental data 54 related to operations of the scanner 12, as discussed below. The memory 32 also includes one or more processor executable instructions that, when executed by the processor 30, coordinate operations of the computer system 28, as well as interfacing with and controlling imaging operations of the scanner 12. The processor 30 executes the processor executable instructions stored in the memory 32.

A first modeling unit 38, which may be part of the system 10 or may be a separate calibration processing system, is configured to generate a first model 39 describing characteristics of the imaging scanner 12. It is to be appreciated that once the normalization model is calculated, it can be used in other scanners with the same detector geometry. That is, the first modeling unit 38 creates a model that simulates the characteristics of the detector geometry of the scanner 12, of which the scanner 12 is a representative sample. It will be appreciated that while depicted in FIG. 1 as a standalone PET scanner 12, the scanner 12 may be an MR/PET scanner, a computed tomography (CT) CT/PET scanner, a single-photon emission computed tomography (SPECT) scanner, or the like. The model generated by the first modeling unit 38, i.e., the "first model", may be a statistical or analytical type of model. In one embodiment, the first model 39 is a statistical radiation transport model, such as a Monte Carlo statistical model, or the like. It will further be appreciated that the first model may be generated using a suitable simulation package, such as GEANT4, GATE, EGS4/EGS5, a standalone equivalent, or the like. The first modeling unit 38 when generating the first model 39 may utilize, for example, the geometry of various components of the scanner 12, e.g., gantry, crystals, shape, size, location, etc. It will be appreciated that the first model 39 may be used to simulate the response of the scanner 12 to a particular source, such as that described with a second model 41.

The system 10 also includes a second modeling unit 40 that is configured to generate a second model 41, the second model 41 describing each detector's response to radiation from a planar source phantom. The second model 41 may be generated with a cylindrical phantom, that is positioned centrally within the scanner 12. Such a cylindrical phantom may be positioned completely parallel to the field of view (FOV) of the gantry of the PET scanner 12. In other embodiments, different source geometries can be used with respect to the model 41, including, for example, rotating line source geometries, cylindrical annulus geometries, etc. Accordingly, it will be appreciated that reference herein to a cylindrical phantom is used for purposes of example. It will also be appreciated that the second modeling unit 40 may enable an associated user to position the source wherever it is needed, as opposed to performing precise physical placement and measurements as currently done. The second model 41, in one embodiment, is implemented as a radiation transport model. The second model 41 is suitably adapted to simulate a phantom in the scanner 12 that is positioned properly within the scanner 12. It will further be appreciated that while depicted as utilizing a radiation transport model, other statistical modeling, analytical modeling, or a combination of such modeling may be used in accordance with the subject disclosure. For example, Monte Carlo modeling, Boltzmann radiation transport modeling, or the like.

Figure 3A:
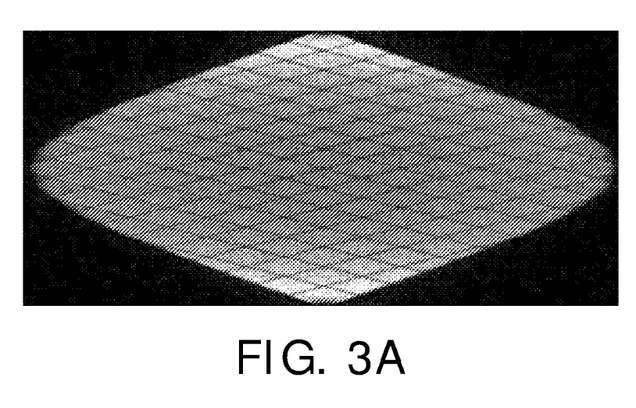
FIG. 3A illustrates a GATE-simulated planar source phantom.
Figure 3B:
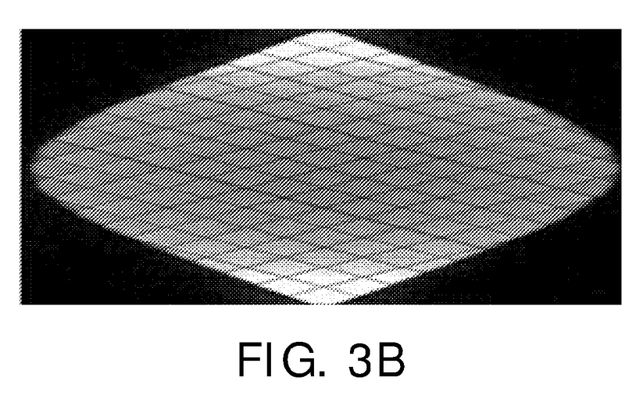
FIG. 3B illustrates experimental data collected of a planar source phantom on a representative PET system.

A normalization data simulator 42 of the system 10 utilizes the first model 39 and the second model 41 to generate a simulated data set corresponding to the scanner 12. According to one embodiment, the normalization data simulator 42 inputs the second model of the planar source detector geometry phantom with activity into the first model 39 corresponding to the characteristics of the scanner 12. The result of the normalization data simulator 42 is a simulated geometrical normalization data set corresponding to the scanner 12. FIG. 3A illustrates a four billion count GATE-simulated planar source phantom as generated in accordance with the subject disclosure (e.g., the simulated planar source detector geometry phantom of the second model input into the first model using a GATE simulation package), whereas FIG. 3B depicts a twenty-five billion count study of a planar source phantom acquired on an existing PET system.

Figure 4A:
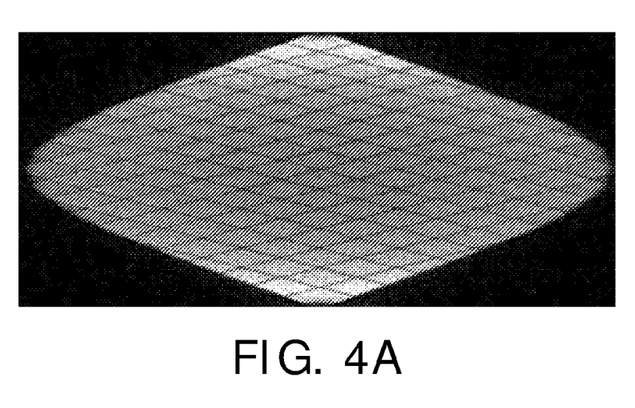
FIG. 4A illustrates a GATE-simulation of a planar source phantom.
Figure 4B:
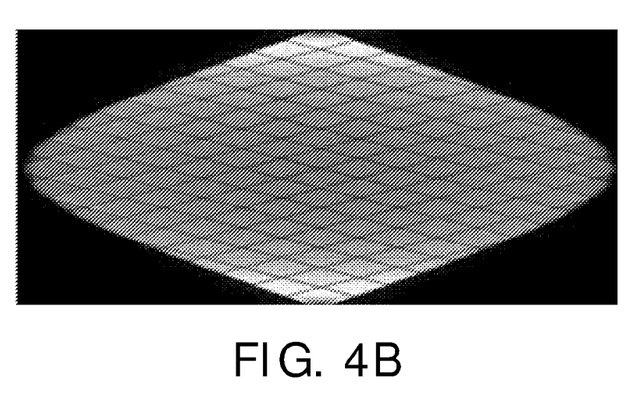
FIG. 4B illustrates the GATE-simulation planar source phantom after de-noising.

In one embodiment, a de-noising unit 48 is utilized to reduce the noise in the simulated normalization data so as to make the correction results more robust. For example, when Monte Carlo type simulations are run, statistical methods, such as principle component analysis (PCA), may be used to reduce the noise. In other embodiments, noise reduction in the simulated normalization data may be performed by the de-noising unit 48 via a variance reduction technique or dimensionality reduction. Such statistical methods may also reduce the cycle time in such Monte Carlo simulations by reducing the number of required counts. FIGS. 4A-4B illustrate before de-noising and after de-noising of simulated normalization data. FIG. 4A illustrates an original GATE-simulation of the planar phantom with four billion counts. FIG. 4B illustrates the GATE-simulation of the planar phantom with four billion counts of FIG. 4A after application of principle component analysis by the de-noising unit 48. As will be appreciated, the de-noising shown in FIG. 4B illustrates the ability of the subject systems and methods to use a limited number of simulation runs while still providing adequate statistics for detector normalization calculations (discussed below).

The system 10 of FIG. 1 further includes a detector geometry correction unit 44 that is configured to utilize the simulated normalization data from the normalization data simulator 42 to generate a detector geometry correction component 67, i.e., a geometrical normalization correction component. It will be appreciated that the detector geometry correction component generated by the correction unit 44 may subsequently be used in any scanner 12 that has the same detector geometry as that modeled by the first modeling unit 38. Thus, for example, all particular models made by the manufacturer that utilize the detector geometry can use the detector geometry correction component. The generation of a detector geometry correction component from the simulated first model 39 can be performed in accordance with the component-based normalization correction methodology set forth in Wang, Hu, and Gagnon, "A New Component Approach Efficiency Normalization for 3D PET," 2005 *IEEE Nuclear Science Symposium Conference Record*, M11-303, 2005, the entirety of which is incorporated by reference herein.

The system 10 further includes a crystal efficiency unit 46 to determine a crystal efficiency component of normalization for the scanner 12. For each individual scanner 12, a measured uniform cylinder filled with activity may be used by the crystal efficiency unit 46 to generate the crystal efficiency component of normalization for each particular scanner 12. In contrast to the detector geometry correction component, the crystal efficiency component must be generated by the crystal efficiency unit 46 for each individual scanner 12, regardless of whether two or more scanners 12 are of the same model or type. That is, as the crystals 20 differ amongst individual scanners 12, the same crystal efficiency component of normalization cannot be used. Furthermore, as the calibration of the crystals 20 may be affected over time, e.g., movement of the scanner 12, jostling, maintenance, regular operations, etc., the crystal efficiency unit 46 may be operated at regular intervals to ascertain a new crystal efficiency component for normalization, and thus calibration of the scanner 12. It will be appreciated that the detector geometry correction component and the crystal correction component together form the normalization correction for a particular scanner 12. The crystal efficiency component for normalization correction may be generated in accordance with the methodology set forth in Wang, as incorporated above.

In accordance with one embodiment, the system 10 depicted in FIG. 1 includes a validation unit 50 that is operative to validate the first model 39, i.e., the simulation model of the scanner 12. The validation unit 50 may utilize experimental data 52 corresponding experimental measurements (averages) that describe the particular model (i.e., scanner 12). The comparison of the first model 39 to the experimental data 52 enables the validation unit 50 to identify any misconceptions, errors, incorrect assumptions, or the like, contained in the first model 39. It will be appreciated that such validation need only be performed on one particular scanner 12 having the detector geometry of the first model 39, thus foregoing the validation operation for all subsequently produced scanners 12 having the same detector geometry.

The system 10 further includes a normalization unit 54 that is configured to generate a normalization data set 56 for a particular scanner 12. The normalization unit 54 receives the detector geometry correction component and the crystal efficiency component to form the normalization correction data set 56, which is used for normalization correction of the individual scanner 12. It will be appreciated that the normalization unit 54 may be implemented subsequent to noise reduction via the de-noising unit 48 and/or after validation via the validation unit 50. In one embodiment, the normalization unit 54 may output the normalization correction data set 56 as a normalization correction factor that is applied to the scanner 12 during manufacture, installation, or maintenance of the scanner 12. In another embodiment, normalization correction factors are stored in a lookup table or other similar structure for retrieval and use during image generation by the system 10.

Each of the typically thousands of detectors 14 should output the same response, e.g., counts, to a given radiation source over a given time. However, due to geometry, some detectors 14 will witness fewer events than others. Similarly, due to scintillator efficiency, some detectors 14 will output more events than others. The normalization correction includes a correction factor for each of the detectors, which are calculated to give uniform responses to all detectors. During PET imaging, pairs of coincidently detected radiation define a line of response (LOR). As the LORs are reconstructed, each is weighted in accordance with normalization correction factors of the pair of detectors 14 that define it.

Referring now to FIG. 5, there is shown a functional block diagram 60 illustrating one embodiment for normalization correction of a scanner 12 in accordance with the systems and methods set forth herein. The first model 39 is generated of the scanner 12 via the first modeling unit 38, shown in FIG. 5 as the Monte Carlo simulation model 61 of a PET/SPECT system 10. This Monte Carlo simulation model 61 describes the characteristics of the PET scanner 12 of interest using a suitable simulation package, as discussed above. The simulation model 61 can be validated against reference experimental measurements (averages) that describe a particular system model. The second model 41 is generated by the second modeling unit 40 to simulate a normalization source, shown in FIG. 5 as the Monte Carlo simulation model 62 of the normalization source. The system model 61 utilizes the normalization source simulation model 62 to simulate PET normalization data so as to obtain sufficient data for further processing.

The embodiment 60 further includes a Monte Carlo de-noising component 64 that implements a statistical method to reduce the noise in the data to render the correction results more robust. Statistical methods, such as PCA, or the like can be used to reduce the cycle time in the Monte Carlo simulations by reducing the number of counts. The simulated data (from the first model 61 using the simulated source of the second model 62) is then subjected to component-based normalization 65, as set forth in Wang et al. This normalization 65 generates the detector geometry correction component that can be used for all scanners 12 with this same detector geometry as that modeled via the first model 61. For each individual scanner 12, a measured uniform cylinder filled with activity is used to generate the crystal efficiency component of normalization. Thus, the embodiment 60 depicted in FIG. 5 outputs a crystal efficiencies normalization component 66 and a geometrical normalization component 67 which together form the normalization correction dataset 68, i.e., the normalization correction for the scanner 12.

Figure 6:
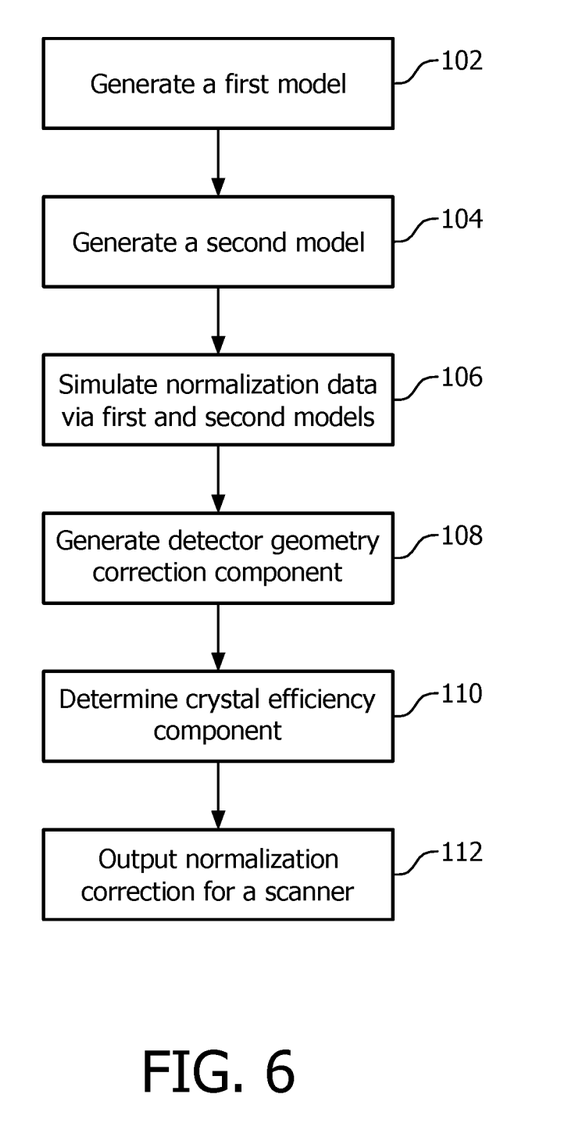

FIG. 6 flowcharts one method 100 of determining normalization correction for an imaging system 10. In step 102, the first model 39 is mathematically calculated based upon the geometrical characteristics of a scanner 12 of interest. In one embodiment, the first model 39 is a radiation transport model that mathematically describes the geometry of the scanner 12, i.e., various components of the scanner 12, various operating characteristics, radiation responses, etc. That is, the first model 39 models the non-uniform response of the detectors 14 due to geometry. The first model 39 may be generated utilizing a particular simulation package, such as, for example, GEANT4, GATE, EGS4/EGS5, or the like.

At step 104, a second model is generated describing a planar source detector geometry for use with the first model 39 in determining normalization correction for the scanner 12 of interest. As described above, the second model 41 may be implemented as a cylindrical phantom that is positioned at a predetermined position or positions within the scanner 12, e.g., parallel to the FOV of the gantry of the scanner 12, or the like. It will be appreciated that the second model 41 may be implemented as other types of sources, including, for example, multiple planar sources at different orientations, point sources through the FOV, or any other suitable configuration from which a detector geometry normalization can be obtained. Accordingly, use of the cylindrical phantom with respect to the second model 41 is referenced herein for example purposes. Although referenced as pertaining to radiation transport models, the first model 39 and second model 41 may be implemented as other statistical models, e.g., Monte Carlo models, analytical models, e.g., Boltzmann, etc., or a combination of the same, e.g., the first model 39 is statistical and the second model 41 is analytical, or the like.

At step 106, normalization data is simulated via the first model 39 and the second model 41. That is, the planar source detector geometry of the second model 41 is input or otherwise used to perform the simulations of the first model 39. The simulated normalization data may be used, at step 108, to generate a detector geometry correction component for the scanner 12 type of interest. As previously discussed, the detector geometry correction component may be used for any subsequent scanner that is of the same type, e.g., same physical characteristics and thus the same model thereof, i.e., the first model 39.

After generation of the detector geometry correction component, the crystal efficiency component corresponding to an individual scanner 12 of the type of scanner of interest is then empirically determined at step 110. That is, as crystals 20 differ across each scanner and between scanners, each scanner has its own distinct crystal efficiency normalization component that is particular to the crystals 20 of the scanner 12. For example, a cylindrical phantom may be used to irradiate the detectors 14 uniformly, such that the non-uniform response of each detector 14 (via crystals 20) is measured. From the non-uniform response, the crystal efficiency normalization component is empirically determined. At step 112, a normalization data set 56, comprising the detector geometry correction component and the crystal efficiency component, is output for normalization correction of the scanner 12. In one embodiment, the detector geometry correction component (geometric normalization) and the crystal efficiency component (detector efficiency corrections) are combined into system normalization correction factors.

Although determining the models 39 and 41 and normalization correction factors has been described with reference to detectors 14, it is to be appreciated that the models 39 and 41 and/or the normalization correction factors can be determined based on LORs. That is, a geometric correction factor can be mathematically simulated for each of the geometrically possible LORs. Similarly, the detector efficiency normalization correction factors can be determined for each of the possible LORs.

As another alternative, the first and second models 39 and 41 are combined and the system normalization correction factors are determined from the combined models.

The system normalization correction factors are stored, e.g., in a lookup table. When imaging a patient, radiation events are detected. Coincident pairs of the detected events define LORs which are reconstructed into an image. During reconstruction, each LOR is weighted with the corresponding system normalization correction factor from an LOR-based system normalization lookup table or from the system normalization correction factors of the two detectors 14 which detected the coincident pair.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, a coprocessor, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, a CRT display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A medical system for normalization correction of an imaging system , comprising:
    a first modeling unit which generates a first model simulating characteristics of a type of scanner of interest;
    a second modeling unit which generates a second model of a planar source detector geometry phantom;
    a normalization data simulator configured to simulate normalization data using the first model and using the second model;
    a detector geometry correction unit configured to mathematically calculate a detector geometry correction component for a type of scanner of interest; and
    a crystal efficiency unit configured to empirically determine a crystal efficiency component for at least one individual scanner using the simulated normalization data;
    a normalization unit which generates a normalization data set corresponding to a normalization correction factor of the at least one individual scanner in accordance with the detector geometry correction component and the crystal efficiency component.

2. The medical system according to claim 1, further comprising:
    a de-noising unit configured to reduce noise in the simulated normalization data via variance reduction or dimensionality reduction.

3. The medical system according to claim 1, wherein at least one of the first model or the second model is a statistical radiation transport model.

4. The system according to claim 1, wherein the first model or the second model is an analytical model or a statistical model.

5. The medical system according to claim 1, wherein the first model and the second model are generated using Monte Carlo simulation models.

6. The medical system according to claim 1, further comprising:
    a validation unit configured to validate the simulated normalization data against experimental data associated with the type of scanner of interest.

7. The medical system according to claim 1, wherein the imaging system is one of a positron emission tomography (PET) imaging system and/or a single-photon emission computed tomography (SPECT) imaging system.

8. A method for normalization correction of an imaging system , comprising:
    generating a first model mathematically describing characteristics of a type of scanner of interest;
    generating a second model of a planar source detector geometry phantom;
    simulating normalization data in accordance with the first model using the second model;
    generating a detector geometry correction component for a type of scanner of interest using the simulated normalization data;
    empirically determining a crystal efficiency component for at least one individual scanner of the scanner type of interest; and
    outputting at least one normalization correction factor for the at least one individual scanner in accordance with the detector geometry correction component and the crystal efficiency component.

9. The method according to claim 8, wherein the first model or the second model is an analytical model or a statistical model.

10. The method according to claim 8, wherein the first model or the second model is a statistical radiation transport model.

11. The method according to claim 8, wherein the first model and the second model are generated using Monte Carlo simulation models.

12. The method according to claim 8, further including:
    reducing noise in the simulated normalization data via variance reduction or dimensionality reduction.

13. The method according to claim 8, wherein reducing the noise in the simulated normalization data uses principle component analysis.

14. A non-transitory computer-readable storage medium carrying software which controls one or more electronic data processing devices to perform the method according to claim 8.

15. An electronic data processing device configured to perform the method according to claim 8.

16. A system , comprising:
    a first model which is mathematically calculated based on geometric characteristics of a type of scanner of interest;
    a second model which is mathematically calculated based on geometry of a calibration phantom; and
    a processor configured to generate normalization correction factors for an individual scanner based on crystal efficiency data collected by the individual scanner from a phantom and the first and second models.

17. The system according to claim 16, further comprising:
    a detector geometry correction unit which calculates the first and second models; and
    a crystal efficiency correction unit which empirically determines the crystal efficiency data for the individual scanner of the scanner type of interest.

* * * * *